United States Patent [19]

Sugavanam

[11] Patent Number: 4,507,140
[45] Date of Patent: Mar. 26, 1985

[54] TRIAZOLE AND IMIDAZOLE COMPOUNDS USEFUL AS FUNGICIDES AND PLANT GROWTH REGULATORS

[75] Inventor: Balasubramanyan Sugavanam, Wokingham, England

[73] Assignee: Imperial Chemical Industries PLC, London, England

[21] Appl. No.: 317,853

[22] Filed: Nov. 3, 1981

[30] Foreign Application Priority Data

| Nov. 19, 1980 [GB] | United Kingdom | 8037103 |
| Jan. 12, 1981 [GB] | United Kingdom | 8100804 |
| Jan. 29, 1981 [GB] | United Kingdom | 8102703 |
| Mar. 23, 1981 [GB] | United Kingdom | 8109024 |
| Jul. 3, 1981 [GB] | United Kingdom | 8120670 |

[51] Int. Cl.³ .................. A01N 43/50; A01N 43/64; C07D 233/60; C07D 249/08
[52] U.S. Cl. .................. 71/76; 71/92; 546/210; 548/101; 548/262; 548/341; 548/336; 514/184; 514/383; 514/396
[58] Field of Search .................. 548/262, 101, 341; 542/400; 424/245, 269, 273 R; 71/76, 92

[56] References Cited

U.S. PATENT DOCUMENTS

| 4,079,143 | 3/1978 | Balasubramanyan et al. | 424/269 |
| 4,167,576 | 9/1979 | Miller et al. | 424/273 R |
| 4,225,723 | 9/1980 | Miller et al. | 548/341 |
| 4,259,339 | 3/1981 | Miller et al. | 424/269 |
| 4,366,165 | 12/1982 | Miller et al. | 424/269 |
| 4,414,210 | 11/1983 | Miller et al. | 548/101 |

FOREIGN PATENT DOCUMENTS

| 867245 | 11/1979 | Belgium | 548/262 |
| 15756 | 9/1980 | European Pat. Off. | 548/262 |
| 15639 | 9/1980 | European Pat. Off. | 548/262 |
| 19189 | 11/1980 | European Pat. Off. | 548/262 |
| 23103 | 1/1981 | European Pat. Off. | 548/341 |
| 33501 | 8/1981 | European Pat. Off. | 548/341 |
| 40345 | 11/1981 | European Pat. Off. | 548/262 |
| 71009 | 2/1983 | European Pat. Off. | 548/262 |
| 3018866 | 11/1981 | Fed. Rep. of Germany | 548/262 |
| 2327242 | 5/1977 | France | 548/262 |
| 2398056 | 2/1979 | France | 548/341 |
| 2434154 | 3/1980 | France | 548/341 |
| 1533748 | 11/1978 | United Kingdom | 548/341 |
| 2064520 | 6/1981 | United Kingdom | 548/262 |

*Primary Examiner*—Alton D. Rollins
*Attorney, Agent, or Firm*—Cushman, Darby & Cushman

[57] ABSTRACT

Fungicidal or plant growth regulating triazoles or imidazoles of the formula

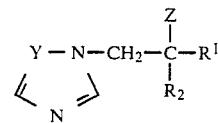

wherein $R^1$ is —CH=CH—X, —C≡C—X or —CH$_2$—CH$_2$—X where X is H, alkyl, hydroxyalkyl, alkoxyalkyl, cycloalkyl or optionally substituted aryl, aralkyl, aryloxyalkyl, or heterocycle; and $R^2$ is alkyl, cycloalkyl (e.g. cyclopropyl, cyclopentyl, or cyclohexyl) or optionally substituted aryl; Z is Cl, CN or $OR^3$ where $R^3$ is H, acetyl, alkenyl or aralkyl; Y is =N— or =CH—; and acid addition salts and metal complexes thereof.

7 Claims, No Drawings

TRIAZOLE AND IMIDAZOLE COMPOUNDS USEFUL AS FUNGICIDES AND PLANT GROWTH REGULATORS

This invention relates to triazole and imidazole compounds useful as fungicides, to a process for preparing them, to fungicidal compositions containing them, and to a method of combating fungal infections in plants using them.

The invention provides triazole and imidazole compounds having the general formula (I):

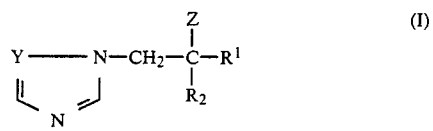
(I)

wherein $R^1$ is —CH=CH—X, —C≡C—X or —CH$_2$—CH$_2$—X where X is H, alkyl, hydroxyalkyl, alkoxyalkyl, cycloalkyl or optionally substituted aryl, aralkyl, aryloxy alkyl, or heterocycle; and $R^2$ is alkyl, cycloalkyl (e.g. cyclopropyl, cyclopentyl, or cyclohexyl) or optionally substituted aryl; Z is Cl or CN or $OR^3$ where $R^3$ is H, acetyl, alkyl, alkenyl or aralkyl; Y is =N— or =CH—; and acid addition salts and metal complexes thereof.

The compounds of the invention can contain geometric isomers. Such compounds are generally obtained in the form of isomeric mixtures. However, these and other mixtures can be separated into the individual isomers by methods known in the art.

The alkyl and alkenyl groups can be a straight or branched chain group having 1 to 6, e.g. 1 to 4, carbon atoms; examples are methyl, ethyl, propyl (n- or iso-propyl) and butyl (n-, sec-, iso- or t-butyl). They can be hydroxy- or alkoxy-substituted.

Examples of suitable substituents for the aryl and heterocycle groups, (the preferred aryl is phenyl and the preferred heterocycle are furyl and pyridyl) are halogen (e.g. fluorine, chlorine or bromine), $C_{1-5}$ alkyl [e.g. methyl, ethyl, propyl (n- or iso-propyl) and butyl (n-, sec-, iso- or t-butyl)], $C_{1-4}$ alkoxy (e.g. methoxy and ethoxy), halo-alkoxy (e.g. trifluoromethoxy), trifluoromethyl, nitro, phenyl and phenoxy. The phenyl ring may be, for example, unsubstituted or substituted with 1, 2 or 3 ring substituents as defined above. Preferably the phenyl has a single ring substituent in the 2-position. Examples of these groups are phenyl, 2-, 3- or 4-chlorophenyl, 2,4- or 2,6-dichlorophenyl, 2-, 3- or 4-fluorophenyl, 2,6-difluorophenyl, 2-, 3- or 4-bromophenyl, 2-chloro-4-fluorophenyl, 2-chloro-6-fluorophenyl, 2-, 3- or 4-methoxyphenyl, 2,4-dimethoxyphenyl, 2-, 3- or 4-ethoxyphenyl, 2-, 3- or 4-nitrophenyl, 2-, 3- or 4-methylphenyl, 2-, 3- or 4-t-butylphenyl, 2-, 3- or 4-trifluoromethylphenyl, 2-, 3- or 4-phenoxyphenyl, and 2-, 3- or 4-phenylphenyl (2-, 3- or 4-biphenylyl).

The invention further provides compounds of the formula (formula I) above wherein X and $R^2$, which may be the same or different, are alkyl or cycloalkyl groups containing from up to 6, especially up to 4, carbon atoms, phenyl, halophenyl, alkylphenyl or alkoxyphenyl.

In a further aspect, the invention provides compounds of formula I above wherein X and $R^2$ are butyl, especially t-butyl, or phenyl optionally substituted at the 2- or 4-positions, or at both positions, with chlorofluoro-, $C_{1-4}$ alkyl, or $C_{1-4}$ alkoxy.

The invention particularly provides triazole compounds as defined above.

The salts can be salts with inorganic or organic acids e.g. hydrochloric, nitric, sulphuric, acetic, 4-toluene sulphonic or oxalic acid.

Suitably the metal complex is one including, as the metal, copper, zinc, manganese or iron. It preferably has the general formula:

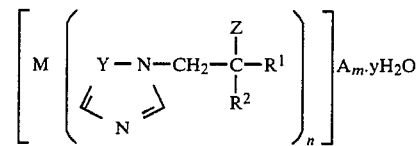

wherein $R^1$ and $R^2$, Z and Y are as defined above, M is a metal, A is an anion (e.g. a chloride, bromide, iodide, nitrate sulphate or phosphate anion), n is 2 or 4, y is 0 or an integer of 1 to 12, and m is an integer consistent with valency.

Examples of the compounds of the invention are shown in Table I. These compounds correspond to the general formulae:

TABLE I formula A

Y—N—CH$_2$—C(OR$^3$)(R$^2$)—CH=CH—X formula B

N—N—CH$_2$—C(OR$^3$)(R$^2$)—C≡C—X formula C

Y—N—CH$_2$—C(OR$^3$)(R$^2$)—CH$_2$—CH$_2$—X

| COMPOUND NO | FORMULA | R$^3$ | R$^2$ | X | Y | MELTING POINT °C. |
| --- | --- | --- | --- | --- | --- | --- |

TABLE I-continued

| | | | | | | |
|---|---|---|---|---|---|---|
| 1 | A | H | t-C$_4$H$_9$ | 2,4-dichlorophenyl | N | 101–103 |
| 2 | A | H | t-C$_4$H$_9$ | 4-chlorophenyl | N | 105–107 |
| 3 | A | H | C$_6$H$_5$ | C$_6$H$_5$ | N | 140–142 |
| 4 | A | H | C$_6$H$_5$ | C$_6$H$_5$ | CH | 204–206 |
| 5 | A | H | C$_6$H$_5$ | 2-chlorophenyl | N | 80–82 |
| 6 | A | H | t-C$_4$H$_9$ | 4-chlorophenyl | CH | 157–159 |
| 7 | A | H | t-C$_4$H$_9$ | 4-fluorophenyl | N | 139–140 |
| 8 | A | H | t-C$_4$H$_9$ | 4-chlorophenyl | CH | 171–172 |
| 9 | A | H | 4-methoxyphenyl | C$_6$H$_5$ | N | 101–103 |
| 10 | A | H | 4-fluorophenyl | C$_6$H$_5$ | N | 102–104 |
| 11 | A | H | t-C$_4$H$_9$ | 2-chlorophenyl | N | 144–145 |
| 12 | A | H | t-C$_4$H$_9$ | t-C$_4$H$_9$ | N | 77–77.5 |
| 13 | A | H | 4-chlorophenyl | 4-chlorophenyl | N | 83–84 |
| 14 | A | H | 4-chlorophenyl | phenyl | N | 81–83 |
| 15 | A | H | 4-chlorophenyl | 4-methoxyphenyl | N | 58–60 |
| 16 | A | H | 4-fluorophenyl | 4-chlorophenyl | N | 58–60 |
| 17 | A | H | 4-chlorophenyl | 4-fluorophenyl | N | 82–84 |
| 18 | A | H | 4-chlorophenyl | 2-chlorophenyl | N | 71–73 |
| 19 | A | H | t-C$_4$H$_9$ | 2-chloro-4-fluoro-phenyl | N | 130.5–132 |
| 20 | B | H | 4-chlorophenyl | phenyl | N | Oil |
| 21 | B | H | t-C$_4$H$_9$ | phenyl | N | 91–92 |
| 22 | B | H | 4-fluorophenyl | phenyl | N | 108 |
| 23 | B | H | phenyl | phenyl | N | 119 |
| 24 | B | H | t-C$_4$H$_9$ | 4-chlorophenyl | N | 127–128 |
| 25 | B | H | t-C$_4$H$_9$ | 2,4-dichlorophenyl | N | 79–80 |
| 26 | A | H | phenyl | 4-chlorophenyl | N | 134–135 |
| 27 | C | H | t-C$_4$H$_9$ | 4-fluorophenyl | N | 94–96 |
| 28 | C | H | t-C$_4$H$_9$ | 4-chlorophenyl | N | 85–86 |
| 29 | C | H | t-C$_4$H$_9$ | 2,4-dichlorophenyl | N | 87–88.5 |
| 30 | A | H | t-C$_4$H$_9$ | 2-fluoro-4-chloro-phenyl | N | 121–122 |
| 31 | A | H | 1-methylcyclopropyl | 4-chlorophenyl | N | 148–149 |
| 32 | A | H | t-C$_4$H$_9$ | 4-methoxyphenyl | N | 88.5–90 |
| 33 | A | H | t-C$_4$H$_9$ | 4-methylphenyl | N | 149–150 |
| 34 | A | CH$_3$ | t-C$_4$H$_9$ | 4-chlorophenyl | N | Oil |
| 35 | A | H | t-C$_4$H$_9$ | 4-cyanophenyl | N | 137–139 |
| 36 | A | H | t-C$_4$H$_9$ | fur-2-yl | N | 97–98 |
| 37 | A | H | t-C$_4$H$_9$ | 4-phenylphenyl | N | 95–97 |
| 38 | A | Allyl | t-C$_4$H$_9$ | 4-chlorophenyl | N | Oil |
| 39 | A | H | 2-fluorophenyl | 4-methylphenyl | N | 123–124 |
| 40 | A | H | 2-chlorophenyl | 4-methylphenyl | N | 124–125.5 |
| 41 | A | CH$_3$ | t-C$_4$H$_9$ | 4-fluorophenyl | N | 58–60 |
| 42 | A | H | t-C$_4$H$_9$ | phenyl | N | 108–109 |
| 43 | A | CH$_3$ | t-C$_4$H$_9$ | 4-methoxyphenyl | N | Oil |
| 44 | A | H | 4-chlorophenyl | fur-2-yl | N | 88–89 |
| 45 | A | H | t-C$_4$H$_9$ | 5-ethylfur-2-yl | N | 88.5–87 |
| 46 | A | H | 2-chlorophenyl | 4-methoxyphenyl | N | 98–100 |
| 47 | A | H | 4-chlorophenyl | 4-methylphenyl | N | 108–109.5 |
| 48 | B | H | t-C$_4$H$_9$ | pyrid-2-yl | N | 145 |
| 49 | B | H | t-C$_4$H$_9$ | —C(CH$_3$)$_2$OH | N | 105–106 |
| 50 | B | H | t-C$_4$H$_9$ | —C(CH$_3$)$_2$OCH$_3$ | N | 60–61 |
| 51 | B | CH$_3$ | t-C$_4$H$_9$ | 4-chlorophenyl | N | 197–198* |
| 52 | B | H | t-C$_4$H$_9$ | 4-methylphenyl | N | — |
| 53 | B | H | 2-fluorophenyl | 4-methylphenyl | N | 145–146 |
| 54 | B | n-C$_4$H$_9$ | t-C$_4$H$_9$ | pyrid-3-yl | N | — |
| 55 | B | H | t-C$_4$H$_9$ | 2,6-dimethyl-4-chloro-(CH$_2$O)phenyl | N | gum |
| 56 | B | H | 4-chlorophenyl | —C(CH$_3$)$_2$OCH$_3$ | N | |

TABLE I-continued

| 57 | B | H | 4-chlorophenyl | t-C$_4$H$_9$ | N |
|----|---|---|----------------|--------------|---|

*N—methyltriazolium salt.

In the foregoing Table compounds Nos 2 and 24 are particularly suitable for the fungi-combating process of the invention.

The compounds of general formula (I) may be produced by reacting a compound of general formula (II) or (III):

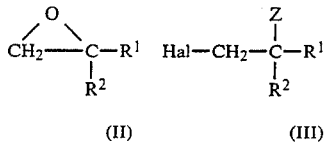

(II)      (III)

in which R$^1$, R$^2$ and Z are as defined above and Hal is a halogen atom (preferably a chlorine or bromine atom), with 1,2,4-triazole or imidazole either in the presence of an acid-binding agent or in the form of one of its alkali metal salts in a convenient solvent. For compounds in which R$^1$ is —CH$_2$—CH$_2$—X the compounds produced by the foregoing process are reduced by catalytic hydrogenation.

Suitably the compound of general formula (II) or (III) is reacted at 20°-100° C. with the sodium salt of 1,2,4-triazole or imidazole (the salt can be prepared by adding either sodium hydride or sodium methoxide to 1,2,4-triazole or imidazole) in a convenient solvent such as acetonitrile, methanol, ethanol or dimethylformamide. The product can be isolated by pouring the reaction mixture into water and recrystallising the solid formed from a convenient solvent.

The ethers (R$_3$=alkyl etc) of the invention are made from the hydroxy compounds by reacting them with the appropriate halide in the pressure of a suitable base.

The compounds of general formula (II) wherein each of R$^1$ and R$^2$ are as defined above are novel and useful intermediates and, per se, form part of the present invention. They can be prepared by reacting the appropriate compound of general formula (IV)

$$R^1—CO—R^2 \quad (IV)$$

wherein R$^1$ and R$^2$ are as defined above, with dimethylsulphonium methylide (Corey and Chaykovsky, JACS, 1962, 84, 3782) using methods set out in the literature.

The α,β-unsaturated ketones of general formula (VI) can be made by condensing the appropriate ketones and aldehydes in the presence of suitable acid or base catalysts.

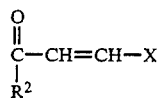

The compounds of general formula (II) and (III) wherein Z is OH can also be prepared by reacting a compound of general formula (IVa) or (IVb):

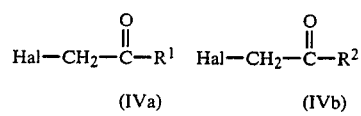

(IVa)      (IVb)

wherein R$^1$, R$^2$ and Hal are as defined above with, respectively, a Grignard compound of general formula (Va) or (Vb):

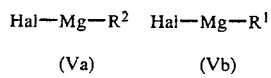

(Va)      (Vb)

wherein R$^1$ and R$^2$ are as defined above and Hal is a halogen (preferably chlorine, bromine or iodine) in a convenient solvent such as diethyl ether or tetrahydrofuran. Generally a mixture of the compounds of general formula (II) and (III) are obtained.

The compounds of general formula (IV) and (V) may be made by methods set out in the literature.

The acetylenic alcohols of the invention can be made by either of the following two schemes:

SCHEME 1

α-1,2,4-triazol-1-yl ketones of the general formula (VI) shown below, and wherein R$_1$ is as defind above are brought into reaction with a metal salt of the appropriate acetylene of general formula (VII) wherein R$_2$ is as defined above, in an inert atmosphere at low temperature and working up the product by quenching with a proton donor.

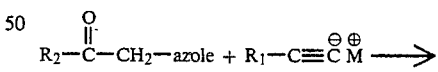

formula (VI)      formula (VII)

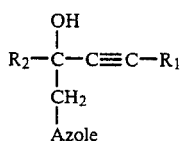

SCHEME 2

An acetylenic ketone of general formula (VIII) is brought into reaction with a sulphur yield of general formula (IX) and the resultant epoxide is brought into reaction with the appropriate azolyl salt.

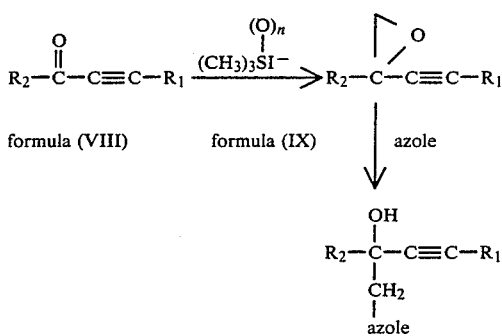

formula (VIII)  formula (IX)  azole

The salts and metal complexes of the compounds of general formula (I) can be prepared from the latter in known manner. For example, the complexes can be made by reacting the uncomplexed compound with a metal salt in a suitable solvent.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber),

*Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: *Fusarium* spp., *Septoria* spp., *Tilletia* spp. (i.e. bunt, a seed borne disease of wheat), *Ustilago* spp., *Helminthosporium* spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds are also useful for the treatment of candidiasis and human dermatophyte infections.

The compounds of the invention, and their derivatives, are also useful for their plant growth regulating effects.

The compounds may be used as such for fungicidal (or plant growth regulating) purposes but are more conveniently formulated into compositions for such usage. The invention thus provides also a fungicidal or plant growth regulating composition comprising a compound of general formula (I) or a salt or complex thereof as hereinbefore defined, and a carrier or diluent.

The invention also provides a method of combating fungal diseases in a plant, which method comprises applying to the plant, to seed of the plant, or to the locus of the plant or seed, a compound or a salt or complex thereof as hereinbefore defined.

The invention also provides a method for regulating plant growth which method comprises applying to the plant, to seed of the plant, or to the locus of the plant or seed, a compound or a salt or complex thereof as hereinbefore defined.

The compounds, salts and complexes can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal activity or compounds having plant growth regulating, herbicidal or insecticidal activity.

The other fungicidal compound can be for example one which is capable of combating ear diseases of cereals (e.g. wheat) such as *Septoria, Gibberella* and *Helminthosporium* spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, fenpropemorph, captafol, captan, sulphur, triforine, dodemorph, tridemorph, pyrazophos, furalazyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

Examples of suitable plant growth regulating compounds are the gibberellins (e.g. $GA_3$, $GA_4$ or $GA_7$, the auxins (e.g. indoleacetic acid, indole-butyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluorecol), maleic hydrazide, glyphosate, glyphosine, long chain fatty alcohols and acids, dikegulac, fluoridamid, mefluidide, substituted quaternary ammonium and phosphonium compounds (e.g. chlormequat or chlorphonium), ethepon, carbetamide, methyl-3,6-dichloranisate, daminozide, asulam, abscissic acid, isopyrimol, 1(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid.

The following Example illustrates the invention; the temperatures are given in degrees Centigrade (°C.).

EXAMPLE 1

This Example illustrates the preparation of 4,4-dimethyl-3-hydroxy-3-(1,2,4-triazol-1-yl)methyl-1(4'-chlorophenyl)-pent-1-ene having the structure

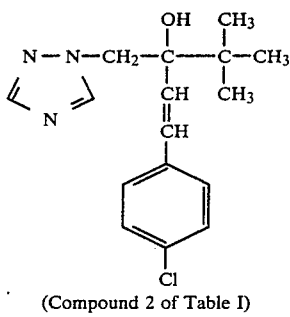

(Compound 2 of Table I)

STAGE I

Preparation of the oxirane of the structure

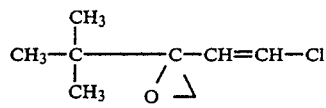

A suspension of NaH(50%) (1.13 parts), prewashed with petroleum ether (40°-60°), in dimethylsulphoxide (40 ml) was heated to 60°-70° for 45 minutes with stirring under nitrogen atmosphere. The mixture was cooled to room temperature, tetrahydrofuran (40 ml) was added, and then cooled to −5°. Trimethylsulphonium iodide (9.6 parts) dissolved in dimethyl sulphoxide (40 ml) was added dropwise over a period of 3 minutes. After stirring for one more minute, t-butyl-4-chlorostyryl-ketone dissolved in tetrahydrofuran (40 ml) was added rapidly to the reaction mixture. After stirring at 0° for 10 minutes, the cooling bath was removed and the reaction mixture was stirred for an additional hour.

The reaction mixture was poured into water (300 ml) and the aqueous solution was extracted with petroleum ether (40°-60°). The organic layer was washed with water, dried (anhydrous $K_2CO_3$) and the solvent was removed to obtain the oxirane as a yellow liquid.

STAGE II

To a suspension a prewashed sodium hydride (50%) (0.81 parts) in dry dimethylformamide (50 ml) was added, dropwise, 1,2,4-triazole (2.33 parts) dissolved in dimethylformamide (20 ml) and the reaction mixture was then kept at 50° for 1 hour. The reaction mixture was thereafter cooled to room temperature and treated with the oxirane (4 parts in 20 ml DMF) prepared as described in Stage I over 30 minutes. After the addition, the reaction mixture was kept at 50° for 2 hours.

The reaction mixture was then poured into water (200 ml) and the solid formed was filtered off. The title compound was crystallised from $CHCl_3$/petroleum ether (60°-80°) m.p. 105°-107°.

Other compounds according to the invention were made in similar manner, especially those listed in Table I.

EXAMPLE 2

This Example illustrates the preparation of 2,2-dimethyl-3-(1,2,4-triazol-1-yl)methyl-5-p-chlorophenyl-pentan-4yn-3-ol having the formula:

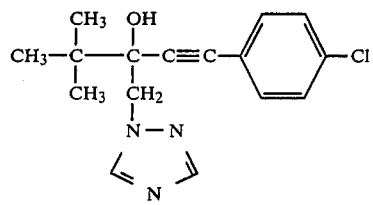

To a solution of p-chlorophenylacetylene (13.78 gg, 0.046 m) in tetrahydrofuran (50 ml) there was added, at −60° with stirring and under nitrogen atmosphere, n-butyllithium (60 ml of a 1.55 m solution, 0.093 m). The reaction mixture was stirred at −70° for one hour and then warmed to 25° and stirred for a further one hour. The dark mixture was cooled to −20° and α-(1,2,4-triazol-1-yl)-pinacolone (7.7 g, 0.046 m) dissolved in tetrahydrofuran (60 ml) was added dropwise. It was then brought to 0° and kept at this temperature for one hour before being allowed to rise to room temperature. It was then treated with saturated aqueous ammonium chloride (15 g in water) solution. The organic layer was separated, the aqueous layer extracted with ether, and the combined organic layers washed with water, dried ($MgSO_4$) and the solvent removed. The title compound was obtained as a solid and was recrystallised from ether, m.p. 127°-128°.

EXAMPLE 3

The compounds were tested against a variety of foliar fungal diseases of plants. The technique employed was as follows.

The plants were grown in John Innes Potting Compost (No 1 or 2) in 4 cm diameter minipots. A layer of fine sand was placed at the bottom of the pots containing the dicotyledonous plants to facilitate uptake of test compound by the roots.

The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:
4=no disease
3=trace-5% of disease on untreated plants
2=6-25% of disease on untreated plants
1=26-59% of diseases on untreated plants 0=60-100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (GRAPE OR TOMATO) | CERCOSPORA ARACHIDICOLA (PEANUT) | VENTURIA INAEQUALIS (APPLE) |
|---|---|---|---|---|---|---|---|---|
| 1 | 4 | 4 | — | 0 | 0 | 3 (grape) | 3 | 0 |
| 2 | 4 | 4 | — | 0 | 0 | 4 (grape) | 4 | 4 |
| 3 | 4 | 4 | — | 0 | 0 | 4 (tomato) | 3 | 4 |
| 4 | 4 | 4 | — | 0 | 0 | 0 (grape) | 3 | 4 |
| 5 | 3 | 4 | — | 0 | 0 | 0 (grape) | 3 | 3 |
| 6 | 4 | 4 | — | 0 | 0 | 0 (grape) | 2 | 0 |
| 7 | 4 | 4 | — | 1 | 0 | 4 (grape) | 4 | 4 |
| 8 | 2 | 4 | — | 2 | 0 | 0 (grape) | 0 | 0 |
| 9 | 2 | 4 | — | 0 | 0 | 0 | 3 | 0 |
| 10 | 4 | 4 | — | 1 | 0 | 0 | 4 | 4 |
| 11 | 2 | 4 | — | 0 | 0 | 0 | 2 | 0 |
| 12 | 4 | 4 | — | 0 | 0 | 0 | 4 | 4 |
| 13 | 4 | 4 | — | 3 | — | 4 | — | 4 |
| 14 | 4 | 4 | — | 2 | — | 0 | — | 4 |
| 15 | 2 | 4 | — | 0 | 0 | 1 | 2 | 2 |
| 16 | 4 | 4 | — | 1 | 0 | 4 | 3 | 4 |
| 17 | — | — | — | — | — | — | — | — |
| 18 | 3 | 4 | — | 0 | 0 | 0 | 3 | 0 |
| 19 | — | — | — | — | — | — | — | — |
| 20 | 3 | 4 | — | 2 | — | 0 | 3 | 3 |
| 21 | 4 | 4 | — | 2 | — | 0 | 4 | 4 |
| 22 | 4 | 4 | — | 2 | — | 0 | 2 | 3 |
| 23 | 3 | 4 | — | 2 | — | — | 3 | 4 |
| 24 | 4 | 4 | — | 0 | — | 0 | 4 | 4 |
| 25 | 4 | 4 | — | 0 | — | 0 | 3 | 4 |
| 26 | 4 | 4 | — | 0 | 0 | 0 | 2 | 3 |
| 27 | — | — | — | — | — | — | — | — |
| 28 | 4 | 4 | — | 1 | 0 | 4 | 4 | 4 |
| 29 | 4 | 4 | — | 0 | 0 | 4 | 3 | 2 |
| 30 | 1 | 4 | — | 0 | — | 0 | 0 | 0 |
| 31 | 4 | 4 | — | 2 | — | 0 | 4 | 4 |
| 32 | 4 | 4 | — | 0 | — | 0 | 4 | 4 |
| 33 | 4 | 4 | — | 0 | — | 0 | 3 | 4 |
| 34 | 4 | 4 | — | 0 | — | 0 | 4 | 4 |
| 35 | 4 | 4 | — | 0 | — | 0 | 3 | 4 |
| 36 | 4 | 4 | — | 0 | — | 0 | 4 | 4 |
| 37 | 3 | 4 | — | 0 | — | 0 | 3 | 4 |
| 38 | 4 | 4 | — | 3 | — | 0 | 4 | 3 |
| 39 | 4 | 4 | — | 0 | — | 0 | 4 | 4 |
| 40 | 4 | 4 | — | 1 | — | 0 | 4 | 3 |
| 41 | 4 | 4 | — | 1 | — | 0 | 3 | 4 |
| 42 | 4 | 4 | — | 1 | — | 0 | 4 | 4 |
| 43 | 4 | 4 | — | 0 | — | — | 3 | 4 |
| 44 | 4 | 4 | — | 0 | — | — | 3 | 4 |
| 45 | — | — | — | — | — | — | — | — |
| 46 | — | — | — | — | — | — | — | — |
| 47 | — | — | — | — | — | — | — | — |
| 48 | 0 | 4 | — | 0 | — | 0 | 0 | 0 |
| 49 | 0 | 4 | — | 0 | — | 0 | 0 | 0 |
| 50 | 4 | 4 | — | 0 | — | — | 3 | 3 |
| 51 | 0 | 4 | — | 3 | — | — | 4 | 1 |
| 52 | 4 | 4 | — | 1 | — | 0 | 4 | 4 |
| 53 | 4 | 4 | — | 0 | — | 0 | 4 | 4 |
| 54 | — | — | — | — | — | — | — | — |
| 55 | — | — | — | — | — | — | — | — |
| 56 | — | — | — | — | — | — | — | — |
| 57 | — | — | — | — | — | — | — | — |

A dash ("—") signifies not tested.

I claim:

1. A triazole compound selected from the group consisting of

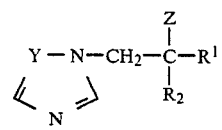

wherein R$^1$ is —C≡C—X where X is alkyl of 1-4 carbons or halophenyl; R$^2$ is alkyl of 1-4 carbons or halophenyl; Z is OR$^3$ where R$^3$ is hydrogen or alkyl of 1-4 carbon atoms; and Y is =N—; and the acid-addition salts and metal complexes thereof.

2. A compound according to claim 1 wherein R$_2$ is chlorophenyl and Z is hydroxy.

3. A compound according to claim 2 wherein Z is OH, X is t-butyl and R$_2$ is 4-chlorophenyl.

4. The compound:

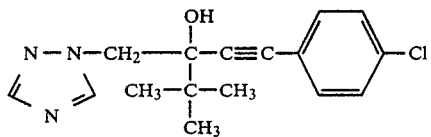

5. A fungicidal composition or plant growth regulating composition comprising, as an active ingredient, an effective amount of a compound, or a salt or metal complex thereof, as defined in claim 1, together with a carrier or diluent thereof.

6. A method of combating fungal diseases in a plant, or regulating the growth of a plant, which method comprises applying to the plant, to seed of the plant, or to the locus of the plant or seed, an effective amount of a compound or a salt or metal complex thereof as defined in claim 1.

* * * * *